US012791558B2

(12) United States Patent
Guiney et al.

(10) Patent No.: US 12,791,558 B2
(45) Date of Patent: Nov. 10, 2026

(54) BIOSENSOR DEVICE AND A METHOD OF MANUFACTURING A BIOSENSOR DEVICE

(71) Applicant: Paragraf Limited, Somersham (GB)

(72) Inventors: Ivor Guiney, Somersham (GB); Elizabeth O'Donovan, Somersham (GB); Simon Thomas, Somersham (GB); Fred Robinson, Somersham (GB)

(73) Assignee: Paragraf Limited, Somersham (GB)

( * ) Notice: Subject to any disclaimer, the term of this patent is extended or adjusted under 35 U.S.C. 154(b) by 874 days.

(21) Appl. No.: 18/101,212

(22) Filed: Jan. 25, 2023

(65) Prior Publication Data

US 2023/0236187 A1 Jul. 27, 2023

(30) Foreign Application Priority Data

Jan. 26, 2022 (GB) ..................................... 2201006

(51) Int. Cl.

*G01N 1/00* (2006.01)
*G01N 33/53* (2006.01)
*G01N 33/543* (2006.01)

(52) U.S. Cl.

CPC ... *G01N 33/54393* (2013.01); *G01N 33/5308* (2013.01); *G01N 33/5438* (2013.01)

(58) Field of Classification Search

None

See application file for complete search history.

(56) References Cited

U.S. PATENT DOCUMENTS

2014/0145148 A1 5/2014 Lee
2017/0307576 A1* 10/2017 Anglin, Jr. ......... G01N 33/0059
2020/0403068 A1* 12/2020 Thomas ............ H01L 21/02205

FOREIGN PATENT DOCUMENTS

WO 2017/029470 A1 2/2017
WO 2019/138232 A1 7/2019
WO 2021/160911 A1 8/2021

OTHER PUBLICATIONS

Kwon et al., "Flexible FET type VEGF Aptasensor Based on Nitrogen Doped Graphene Converted From Conducting Plymer," (2012), ACS Nano, vol. 6, pp. 1486-1493.

Sheng, et al., "Catalyst Free Synthesis of Nitroen Doped Graphene via Thermal Annealing Graphite Oxide with Melamine and its Excellent Electrocatalysis," (2011), ACS Nano, vol. 6, pp. 4350-4358.

Tsang et al., "Chemically Functionalised Graphene FET Biosensor for the Label Free Sensing of Exosomes," (2019), Scientific Reports, vol. 9, No. 13946, pp. 1-10.

(Continued)

*Primary Examiner* — Jyoti Mutreja

(74) *Attorney, Agent, or Firm* — Stinson LLP

(57) ABSTRACT

There is provided a biosensor device comprising: a doped graphene layer structure having at least first and second electrical contacts and a sample-surface between said electrical contacts for receiving an analyte composition to be tested; wherein the doped graphene layer structure is doped with nitrogen and/or phosphorus atoms in an amount of from 1 at % to 10 at %; and wherein the sample-surface is functionalised with a plurality of analyte-receptors, each analyte-receptor being bound to a nitrogen or phosphorus atom of the doped graphene layer structure by a covalent linker moiety.

20 Claims, 2 Drawing Sheets

(56) References Cited

OTHER PUBLICATIONS

Bollella, et al., “Biosensors—Recent Advances and Future Challenges, (MDPI),” (2020), Sensors, vol. 20, No. 6645, pp. 1-5.
Naresh, et al., “A Review on Biosensors and Recent Development of Nanostructured Materials-Enabled Biosensors,” (2021), Sensors, vol. 21, No. 1109, pp. 1-35.
Berchmans, et al., “Immobilization of Molecular Assemblies on 2D Nanomaterials for Electrochemical Biosensing Applications,” (2021) Immobilization Strategies, Springer Link, Book pp. 435-474, Abstract only.
Bai, et al. “Graphene-Based Biosensors for Detection of Biomarkers,” (2020), Micromachines, vol. 11, No. 60, pp. 1-19.
Hugo, A., “Graphene-Based Liquid-Gated Transistors for Biosensing”, (2020), Biological Physics, Université Grenoble Alpes English)). Abstract only.
Georgakilas, et al., “Functionalization of Graphene: Covalent and Non-Covalent Approaches, Derivatives and Applications,” (2012) Chemical Reviews, vol. 112, pp. 6156-6214.
Shin, et al., “Gold Nanoparticle-Mediated Non-Covalent Functionalization of Graphene for Field-Effect Transistors,” (2021), Nanoscale Advances, vol. 3, pp. 1404-1412.
Wang, et al., “Nitrogen-Doped Graphene and Its Application in Electrochemical Biosensing,” (2010), ACS Nano, vol. 4, No. 4, pp. 1790-1798, Abstract only.
Seo, et al., “Rapid Detection of COVID-19 Causative Virus (SARS-CoV-2) in Human Nasopharyngeal Swab Specimens Using Field-Effect Transistor-Based Biosensor,” (2020), ACS Nano, vol. 14, pp. 5135-5142.

* cited by examiner

BIOSENSOR DEVICE AND A METHOD OF MANUFACTURING A BIOSENSOR DEVICE

CROSS-REFERENCE TO RELATED APPLICATIONS

The present application claims priority to Great Britain Patent Application No. 2201006.0, filed Jan. 26, 2022, the entire disclosure of which is incorporated herein by reference.

FIELD OF THE INVENTION

The present invention relates to a biosensor device comprising a graphene layer structure, more particularly a doped graphene layer structure. The present invention also relates to a method of manufacturing a biosensor device, in particular a biosensor device comprising a doped graphene layer structure.

BACKGROUND

Biosensors are well known devices whose importance in modern society have grown rapidly over the last couple of decades. Biosensors are important devices as tools for medical diagnoses as well as in the monitoring of diseases, including cancers and infectious diseases such as Sars-CoV-2 (COVID-19) and sepsis, and drug discovery, together with applications in safety, such as food and environmental monitoring.

Biosensors are often the subject of extensive review. Examples of which include the special issue published in *Sensors* "Biosensors—Recent Advances and Future Challenges" (MDPI) and even more recently, "A Review on Biosensors and Recent Development of Nanostructured Materials-Enabled Biosensors" (*Sensors* 2021, 21, 1109). A biosensor is a device which generates a signal in response to a biological or chemical interaction with an analyte to be measured. A typical biosensor comprises a bioreceptor, transducer, electronics and a display, so as to measure the analyte (i.e. the substance of interest which is to be detected). There are many different conventional configurations of such components. In some systems, they may be integrated within a single apparatus, or the biosensor might form part of a system which includes a separate reader that has the display and carries out the diagnosis. Alternatively, in other systems, a cloud-based service is for data analysis/diagnosis and a remote computer provides the diagnosis and display. A bioreceptor (or an analyte-receptor) is a molecule or other biological element or species that serves to recognise the analyte. Bioreceptors include, though are not limited to, enzymes, cells, aptamers, DNA, RNA and antibodies. The interaction between the analyte and bioreceptor is also known as biorecognition and the biorecognition event (such as a change of light, heat, pH, charge or mass) is a form of energy which is then converted to a measurable signal by the transducer. The electronics serve to process and prepare the transducer signal for display by the display to a user. For example, a processor or a signal processing unit can process a voltage signal generated by the transducer by signal conditioning, such as by amplification and conversion of signals from analogue into the digital form. The processed signals are then quantified by the display unit of the biosensor. Such processing can take place remotely. The user of the biosensor device may be different to the user who analyses the output.

Graphene has found particular applicability in the fabrication of biosensors as a transducer material. Graphene is advantageous in view of its large surface area, electrical conductivity, high charge transfer rate and, most importantly, sensitivity resulting from its unique band structure as a two-dimensional material. Similarly, other two-dimensional materials have also been investigated for use in biosensor devices. For the biorecognition event to be converted into a signal, the bioreceptor needs to be immobilised on the graphene surface for which there are a number of techniques used in the art.

The inventors have found that known methods for immobilisation of suitable bioreceptors on graphene have proven to be a challenging stumbling block in the further development of improved graphene-based biosensors. Recent reviews of immobilisation techniques on graphene and other 2D nanomaterials for biosensors include that published in *Immobilization Strategies* "Immobilization of Molecular Assemblies on 2D Nanomaterials for Electrochemical Biosensing Applications" (Springer, Singapore 2021) as well as "Graphene-Based Biosensors for Detection of Biomarkers" (*Micromachines* 2020, 11, 60).

Further, known graphene immobilisation techniques are outlined in two recent theses related to graphene biosensors (Deana Kwong Hong Tsang "Chemically Functionalised Graphene Biosensor for the Label-free Sensing of Exosomes" (Department of Materials, Imperial College London 2019) and Adrien Hugo "Graphene-based liquid-gated transistors for biosensing" (Biological Physics, Université Grenoble Alpes 2020 English)).

Both Tsang and Hugo review both covalent and non-covalent functionalisation of graphene for use in biosensors. These functionalisation techniques are as described in earlier publications (for example as disclosed in "Functionalization of Graphene: Covalent and Non-Covalent Approaches, Derivatives and Applications" (*Chem. Rev.* 2012, 112, 6156)). Known covalent functionalisation techniques rely on highly reactive intermediates so as to form covalent bonds to graphene. For example, graphene may be functionalised by reaction with 4-nitrophenyldiazonium tetrafluoroborate. Upon liberation of nitrogen gas to yield a reactive radical intermediate, this covalently bonds to an $sp^2$ carbon atom of the graphene sheet generating an $sp^3$ centre. Such methods result in a remarkable decrease in the conductivity and charge carrier mobility due to the disruption. Other similar techniques include those based on highly reactive nitrene intermediates.

By way of example, one of the most recent reports to attempt to address the problems with covalent functionalisation is provided in WO 2021/160911 A1 which discloses a process for obtaining covalently modified graphene, the process comprising applying an electric voltage of at least 10 volts generating an electric field in an area of the graphene surface in the presence of water and a substance that, in water, or in water and in the presence of the electric field generated by said voltage, gives rise to one or more ions and/or one or more radicals.

In view of the drawbacks associated with covalent functionalisation, the most prominent method for functionalising an otherwise atomically flat two-dimensional material simply involves immobilisation via non-covalent van der Waals interactions and 71-71 stacking. For example, "Gold nanoparticle-mediated non-covalent functionalization of graphene for field-effect transistors" (Nanoscale Adv. 2021, 3, 1404) discloses deposition of gold nanoparticles onto a graphene surface as a non-covalent means for attaching a bioreceptor. The gold nanoparticles were then functionalised with a thiol self-assembled monolayer using 4-mercaptobenzoic acid (4-MBA). Other examples include the direct immobilisation of, for example, glucose oxidase (GOx) on a graphene surface by immersing a nitrogen-doped graphene-chitosan electrode in a solution containing the enzyme ("Nitrogen-Doped Graphene and Its Application in Electrochemical Biosensing" (*ACS Nano* 2010, 4, 4, 1790)). One of the most common methods based on the reliable π-π stacking utilises 1-pyrenebutyric acid N-hydroxysuccinimide ester (PBASE) such that graphene-based biosensors have been developed using such technology.

For example, these methodologies allowed for the rapid development of a graphene-based biosensor (specifically a gFET biosensor) effective for the detection of COVID-19 whereby the SARS-CoV-2 spike antibody served as the bioreceptor, conjugated to the graphene sheet via a PBASE linker moiety ("Rapid Detection of COVID-19 Causative Virus (SARS-CoV-2) in Human Nasopharyngeal Swab Specimens Using Field-Effect Transistor-Based Biosensor" (*ACS Nano* 2020, 14, 5135)).

"Flexible FET-type VEGF Aptasensor Based on Nitrogen-Doped Graphene Converted from Conducting Polymer" (*ACS Nano* 2012, 6, 2, 1486) relates to graphene-based FET formed from polypyrrole-converted nitrogen-doped few-layer graphene grown on a Cu substrate with which anti-vascular endothelial growth factor (VEGF) was integrated into a liquid-ion gated FET geometry.

"Catalyst-Free Synthesis of Nitrogen-Doped Graphene via Thermal Annealing Graphite Oxide with Melamine and Its Excellent Electrocatalysis" (*ACS Nano* 2011, 5, 6, 4350) relates to synthesis of nitrogen-doped graphene using melamine as the nitrogen source.

"Chemically Functionalised Graphene FET Biosensor for the Label-free Sensing of Exosomes" (*Scientific Reports* 2019, 9, 13946) relates to a graphene field-effect transistor (gFET) non-covalently functionalised with 1-pyrenebutyric acid N-hydroxysuccinimide ester and conjugated with anti-CD63 antibodies for the label-free detection of exosomes.

US 2014/145148 A1 relates to a field effect transistor using a channel layer including a phosphorus-doped graphene and a method of fabricating the same.

Despite the efforts in the art to develop more sensitive biosensors, there are many challenges which remain. In particular, there still remains a need for a method which allows for the large-scale production of graphene-based biosensors which exhibit the desired sensitivity and reliability for effective use as a biosensor device. The inventors devised the present invention with the aim of overcoming these problems in the prior art, and to at least provide a commercially useful alternative.

SUMMARY OF THE INVENTION

In a first aspect of the present invention, there is provided a biosensor device comprising: a doped graphene layer structure having at least first and second electrical contacts and a sample-surface between said electrical contacts for receiving an analyte composition to be tested; wherein the doped graphene layer structure is doped with nitrogen and/or phosphorus atoms in an amount of from 1 at % to 10 at %; and wherein the sample-surface is functionalised with a plurality of analyte-receptors, each analyte-receptor being bound to a nitrogen or phosphorus atom of the doped graphene layer structure by a covalent linker moiety.

BRIEF DESCRIPTION OF THE FIGURES

The present invention will be described with reference to the following non-limiting Figures, in which.

DETAILED DESCRIPTION OF THE INVENTION

Figure 1:
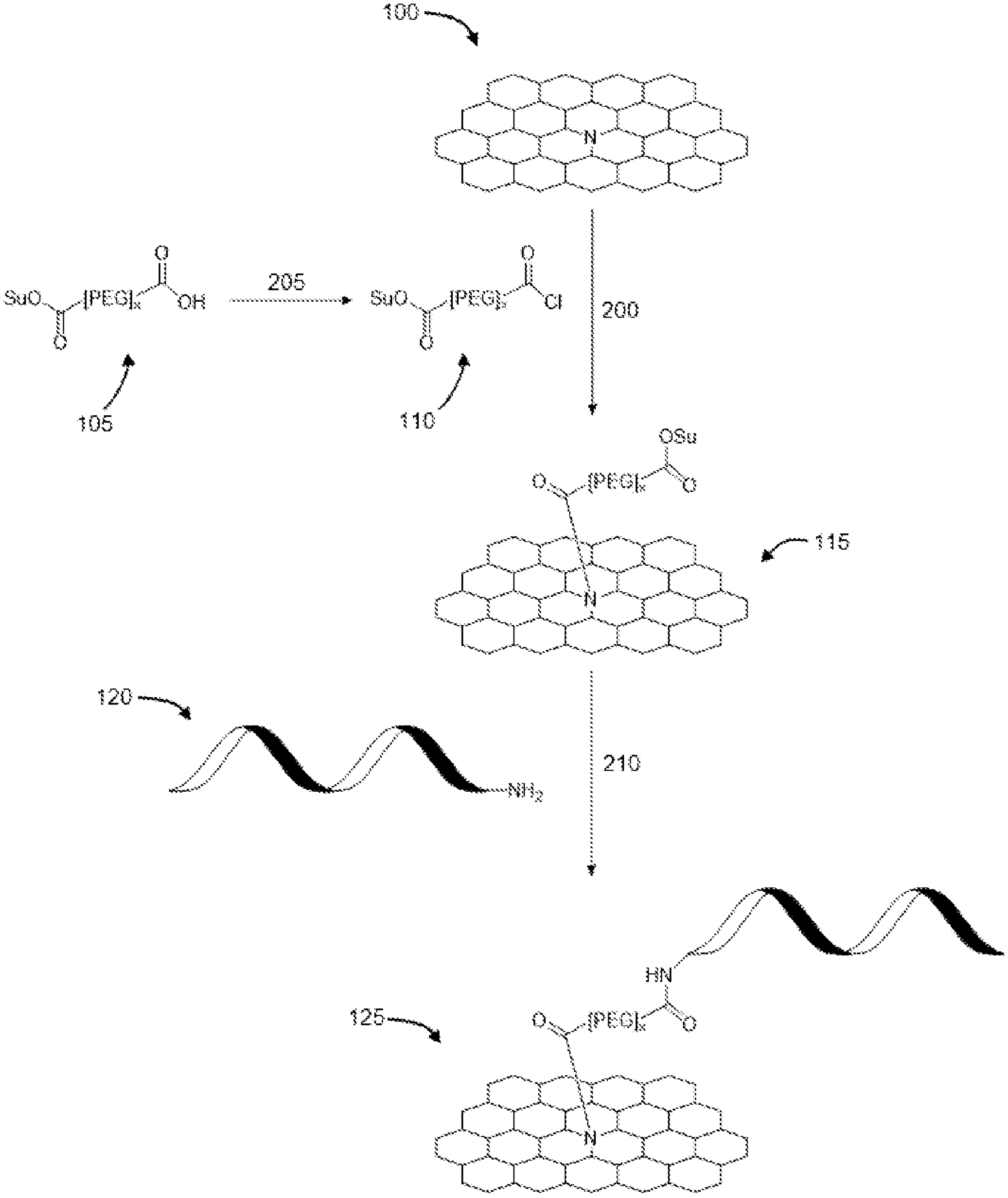
FIG. 1 illustrates a method of covalently functionalising a nitrogen-doped graphene monolayer with a DNA-based analyte-receptor and FIG. 2 illustrates the different types of nitrogen species in nitrogen doped graphene.

The present disclosure will now be described further. In the following passages, different aspects/embodiments of the disclosure are defined in more detail. Each aspect/embodiment so defined may be combined with any other aspect/embodiment or aspects/embodiments unless clearly indicated to the contrary. In particular, any feature indicated as being preferred or advantageous may be combined with any other feature or features indicated as being preferred or advantageous.

The present invention relates to a biosensor device comprising a doped graphene layer structure (which may be referred to herein as a doped graphene layer, doped graphene, or simply graphene). Whilst described in greater detail with respect to the method of manufacture, a graphene layer may be used to refer to the as-deposited graphene which may then be patterned into any desired shape and configuration for a biosensor. The biosensor device provides the bioreceptor and transducer. The biosensor device may be integrated within a biosensor (i.e. a biosensor apparatus) which comprises the necessary electronics and display for processing and displaying an output which allows determination of whether or not a sample composition comprises a predetermined analyte. Alternatively, the biosensor device may be used in connection with the necessary electronics and display (i.e. wired or wirelessly; directly or remotely) as part of a system.

The biosensor has at least first and second electrical contacts provided in electrical connection with said graphene layer structure. The arrangement of such contacts is well-known in the art and serves to define a sample-surface of the graphene layer structure for receiving an analyte composition. That is, an analyte composition is that which is to be tested and provides the analyte dispersed therein (typically a solution). For example, an analyte composition may be blood, saliva, urine, or a diluted solution thereof. As will be appreciated, a biosensor is for testing and detecting the presence of such an analyte and a lack of response will provide the user with a negative result indicating the lack of analyte in the sample composition being tested.

Preferably, the first and second electrical contacts are provided so as to contact at least an edge of the graphene layer structure, thereby separating the first and second contacts by the graphene layer structure surface therebetween. In some preferred embodiments so as to maximise the functional surface area of the graphene layer structure, and so as to minimise undesired doping, the contacts are provided in contact with the graphene layer structure only at an edge. Edge contacts are found to provide more efficient charge injection into the two-dimensional material. The doped graphene layer structure is doped with nitrogen and/or phosphorus atoms in an amount of from 1 at % to 10 at %. That is, the total amount of nitrogen (N) and/or phosphorus (P) atoms present as a substitutional dopant is from 1 at % to 10 at %. The inventors have found that these levels of doping are optimised for the covalent functionalisation as described herein. Preferably, the graphene is doped with at least 2 at % N and/or P since this increases the amount of functionalisation present so as to increase the concentration of possible binding sites to increase device sensitivity. More preferably, the graphene is doped with at least 3 at % N and/or P. On the other hand, the inventors have found that there is an upper limit as to the effective amount of doping before the properties of the functionalised two-dimensional material are unduly negatively affected by the disruption to the $sp^2$ hybridised structure. In particular, 10 at % provides an upper limit, which is preferably at most 7.5 at %, more preferably at most 5 at %. Accordingly, it is preferred that graphene is doped with N and/or P in an amount of from 2 at % to 7.5 at %, preferably from 3 at % to 5 at %. The amount of dopant can be measured using conventional techniques in the art such as transmission electron microscopy (TEM), electron energy loss spectroscopy (EELS) and time-of-flight secondary ion mass spectrometry (ToF SIMS). X-ray photoelectron spectroscopy (XPS) is preferred.

These ranges provide for a covalently functionalised graphene with the desirable electronic properties resulting from the two-dimensional structure of graphene together with an even distribution of analyte-receptors. This is particularly true where the graphene is provided by CVD as described herein since this provides for a uniform distribution of dopant in a high-quality doped graphene layer structure (which may be detected by ToF SIMS). That is the graphene layer structure avoids contamination from transfer processing techniques wherein the catalytic metal (often copper) substrate dopes the graphene with copper atoms and the damaging etching solutions and residual polymers used to transfer the graphene are detrimental to the electronic properties. This is discussed in greater detail in respect of the method which gives rise to the unique product described.

Without wishing to be bound by theory, the inventors have found that another advantage of binding directly to a dopant atom in the plane of the graphene layer structure is that the reduction in distance from the recognition molecule to the transducer helps to overcome the Debye screening length so as to improve the device sensitivity. This is a common problem with known electronic biosensors.

Consequently, it is also preferred that the biosensor device further comprises a non-metallic substrate, wherein the doped graphene layer structure is provided on the substrate. More particularly, it is preferred that the doped graphene layer structure is obtained by CVD growth directly on the substrate, preferably using a carbon-containing precursor comprising nitrogen. It can be determined whether or not a graphene layer structure has been formed by CVD or by a transfer method, since the latter leads to a high number of impurities and defects, and typically includes metal contamination from the metal-catalysed growth procedure.

It is also preferred that the substrate comprises silicon, silicon carbide, silicon nitride, silicon dioxide, sapphire, hafnium dioxide, yttria-stabilised zirconia, magnesium aluminate, yttrium orthoaluminate, strontium titanate, calcium difluoride, germanium and/or a III/V semiconductor. Preferably at least the growth surface on which the graphene is formed comprise these materials and preferably the entire substrate comprises these materials. Such substrates are particularly suitable for high-quality graphene growth directly thereon, especially by the method referred herein (including that disclosed in WO 2017/029470).

Graphene is a very well-known two-dimensional material referring to an allotrope of carbon comprising a single layer of carbon atoms in a hexagonal lattice. Graphene layer structure as used herein, refers to one or more monolayers of graphene. Accordingly, the device encompasses those having a monolayer of graphene as well as multilayer graphene. Preferably, graphene refers to a graphene layer structure having from 1 to 10 monolayers of graphene. A monolayer of graphene is particularly preferred in view of the unique electronic properties associated with the "Dirac cone" band structure of a single graphene sheet. Nevertheless, multilayer graphene may also be preferred, such as 2 or 3 layers of graphene which permits modulation of the band gap.

The sample-surface is functionalised with a plurality of analyte-receptors, each analyte-receptor being bound to a nitrogen or phosphorus atom of the doped graphene layer structure by a covalent linker moiety. That is, a linker moiety is provided covalently bonded to a nitrogen or phosphorus atom of the doped graphene layer structure. The sample-surface comprises a plurality of said linker moieties, each linker moiety is independently covalently bonded to a nitrogen or phosphorus atom of the doped graphene. It is via the covalently bonded linker moiety that the analyte-receptor is bound to the sample-surface. That is, different portions of the linker moiety (typically distal positions of a substantially linear chain, such as a linear hydrocarbon) attach to the dopant element and analyte-receptor. The linker may include one or more functional groups resulting from the covalent attachment with the dopant element and, at the other position, with the analyte-receptor. For example, as described herein, covalent attachment to the graphene surface via the nitrogen atom may give rise to an amide functionality. Similarly, at the distal end of a linear hydrocarbon or a linear polyethylene glycol moiety may be a carboxylic acid functionality. Standard chemical techniques may be used to functionalise the linker moiety with the desired analyte-receptor (which may be a biomolecule such as an enzyme, antibody or antigen).

It is preferred that the graphene layer structure is doped with either nitrogen or phosphorus since such doped graphene is easier to synthesise in part due to the availability of suitable precursors. Both nitrogen and phosphorus are group 15 elements which have one extra electron in their outer valence shell which permit covalent functionalisation at said dopant elements. Nitrogen is a particularly preferred doping element since suitable precursors are more readily available and, more importantly, nitrogen is of a similar size to carbon which facilitates substitutional doping of graphene (i.e. the replacement of a carbon atom for a nitrogen atom). Consequently, it is preferred that the doping consists of nitrogen atoms.

Furthermore, it is preferred that the graphene layer structure consists substantially of carbon and nitrogen and/or phosphorus. Accordingly, it is preferred that the graphene layer structure is not obtained by reduction of graphene oxide which inevitably is contaminated with various oxygen based impurities (hydroxyl and epoxy groups). Furthermore, such techniques also result in highly defective graphene layers resulting from the physical manipulation required to obtain graphene via such route. This does not give rise to the preferred substantially flat sample-surface obtainable by the method disclosed herein. It follows that it is preferred that the graphene layer structure comprises less than 1 at % oxygen (O), preferably less than 0.5 at % oxygen, more preferably less than 0.1 at % oxygen. Similarly, it is preferred that the graphene does not comprise any other dopants, i.e. less than 1 at % total of any other elements (in particular elements except those discussed herein). However, in some embodiments, it may be preferable that the doped graphene layer structure is also doped with other elements so as to provide a desirable charge carrier density. For example, the graphene layer structure may comprise one or more of magnesium (Mg), zinc (Zn), boron (B) and bromine (Br) in a total amount of no more than 5 at %, preferably no more than 3 at %, for example from 1 at % to 3 at %. When the graphene layer structure comprises one or more of magnesium (Mg), zinc (Zn), boron (B) and bromine (Br), preferably the graphene does not comprise any other dopants, i.e. less than 1 at % total of any other elements (in particular elements except those discussed herein).

Nitrogen is a particularly electronegative element which favours the use of nitrogen as an element for covalent functionalisation reactions. As described herein, a linker moiety provided by reacting a linker precursor molecule is typically an organic molecule having carbon-based functionalities and reactive groups so as to provide the covalent functionalisation between the dopant element and carbon. Nitrogen-carbon bonds are also particularly strong providing a robust surface functionalisation such that nitrogen is a preferred dopant.

Figure 2:
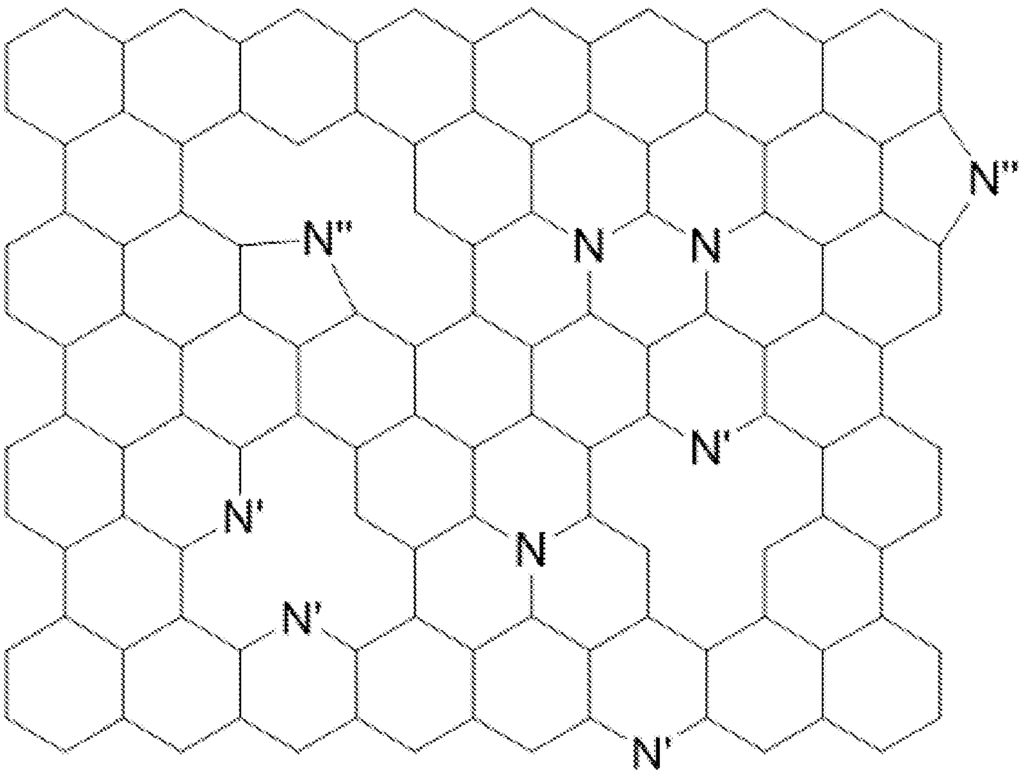

Doping of nitrogen and phosphorus in graphene is known to occur in multiple forms. The structure of doped graphene will be described for nitrogen though applies equally for phosphorus. The different types of nitrogen species in doped graphene is illustrated in FIG. 2. The predominant nitrogen species in nitrogen doped graphene are graphitic, pyridinic and pyrrolic nitrogen. Preferably, a majority of the doping element (i.e. at least 50 at %) is pyridinic and/or pyrrolic nitrogen, preferably pyridinic nitrogen. More preferably, it is at least 75 at %, at least 90 at % or more preferably consists essentially of pyridinic and/or pyrrolic nitrogen. Without wishing to be bound by theory, such nitrogen species are more readily functionalised due to the nitrogen valency and being two coordinate. The amounts of each species may readily be determined by XPS.

Whilst the present invention is described with respect to doped graphene layer structure, it will be appreciated that equivalent two-dimensional materials may also be used in its place so as to achieve substantially the same effect. In particular, silicene (a silicon equivalent to graphene) may be used which again may be doped with either N and/or P atoms for covalent functionalisation sites. Black phosphorus is an all-phosphorus equivalent to graphene (also referred to as phosphorene). Obviously, the presence of phosphorus atoms precludes the requirement for the doping elements for functionalisation. As described for graphene, monolayer silicene, monolayer phosphorene and monolayer TMDCs such as $MoS_2$ are preferred two-dimensional materials for a biosensor device.

In a preferred embodiment, each linker moiety is covalently bonded to the nitrogen via a carbonyl group thereby forming an amide functional group. Typical amide synthesis techniques may be used as a means for covalently attaching the linker moiety to the nitrogen atom of the graphene layer structure. This may be achieved by reacting a linker precursor molecule as described herein with the doped graphene. For example, suitable linker precursor molecules includes those which comprise an acyl or alkyl halide. Preferred linker precursor molecules comprise a spacer group, preferably a substantially linear spacer group such as a linear hydrocarbon, optionally wherein a $CH_2$ group or two or more non-adjacent $CH_2$ groups are replaced by an oxygen, with distal functional groups. The functional groups are preferably carboxylic acids or, may comprise a carboxylic acid and an activated carbonyl group; the activated carbonyl group reacts with the nitrogen in the graphene layer structure to form an amide leaving the carboxylic acid unreacted. For example, an activated carbonyl group may be an activated ester comprising N-hydroxysuccinimide ester. Such a group in known in the art as part of PBASE for non-covalent functionalisation of graphene.

It is also preferred that the spacer group (i.e. spacer moiety) of the linker moiety connecting the two functional groups for attaching to the dopant element and bioreceptor is a polyglycol, preferably polyethylene glycol (PEG). The number of ethylene glycol units is preferably less than 5, such as 1 or 2 (i.e. PEG1 or PEG 2). Preferably, a spacer group such a linear hydrocarbon optionally substituted with oxygen atoms, will have a length of less than 10 atoms (i.e. carbon atoms, and oxygen atoms where present), preferably less than 5. Such a length is preferred in order to bring the analyte close to the graphene surface increasing biosensor sensitivity. As will be appreciated, the spacer may connected to the functional groups via, for example, an oxygen atom giving rise, in the cases described herein resulting in the formation of an amide, the functional group may be a carbamate. In other embodiments, the polyglycol spacer is connected to one or both amide functional groups via a —$CH_2$—$CH_2$— group. One preferred linker precursor molecule is therefore SuO-$[PEG]_x$—COOH, wherein "Su" is N-succinimide ($(CH_2)_2(CO)_2N$—), "PEG" is polyethylene glycol (—$CH_2$—$CH_2$—O—) and x is from 1 to 10. One preferred variant of the activated carbonyl group is an ester comprising sulfo-N-succinimide ($Na(SO_3)(CH_2)_2(CO)_2N$—). Standard coupling reagents may be used for reacting such a precursor molecule with the dopant atom of the graphene layer structure. For example, this can involve the transformation of the carboxylic acid to an acyl halide (typically an acyl chloride) in the presence of a base. The N/P dopant atoms of the graphene will readily react with the acyl halide to form a covalent bond.

Preferably, each analyte-receptor is covalently bonded to the linker moiety, preferably via an amide functional group. Analyte-receptors such as enzymes and antibodies can be coupled with the previously unreacted carboxylic acid functional group using standard organic chemistry techniques. For example, amide coupling syntheses are preferred relying on the presence of a "free" amine group in the biomolecule.

The biosensor device has so far been described with reference to a single doped graphene layer structure having at least first and second electrical contacts and a sample-surface between said electrical contacts for receiving an analyte composition to be tested. This may be referred to as a biosensor cell. In a preferred embodiment, the biosensor device comprises one or more further doped graphene layer structures, each a sample-surface between their electrical contacts for receiving an analyte composition to be tested. In other words, it is preferred that the biosensor device comprises two or more biosensor cells.

Such an arrangement may be referred to a multiplex of sensors (multiplexing). In use, the sample surface of each biosensor cell of the biosensor device is contacted with the common analyte composition to be tested. The sample surface of the graphene layer structure of each biosensor cell may be functionalised with the same analyte-receptor. This is advantageous for improving the reliability of the signal output due to the presence of multiple sensors. In other embodiments, the sample surface of one or more biosensor cells may be functionalised with a different analyte-receptor to the first allowing for the simultaneous detection of two (or more) analytes of interest in a single sample. Microfluidics and/or physical structures may be used to distribute the sample across the sample surfaces.

In another aspect of the present invention there is provided a method of manufacturing a biosensor device, the method comprising:

- forming a doped graphene layer on a substrate, the graphene layer doped with nitrogen and/or phosphorus atoms in an amount of from 1 at % to 10 at %;
- patterning the doped graphene layer to form a doped graphene layer structure;
- providing at least first and second electrical contacts on the doped graphene layer structure to define a sample-surface between said electrical contacts; and
- functionalising the doped graphene layer structure by:
  - (i) reacting the doped graphene layer structure with a plurality of linker precursor molecules to covalently bond each linker precursor molecule to a nitrogen or phosphorus atom of the doped graphene layer structure; and
  - (ii) reacting the covalently bonded linker precursor molecules with a plurality of analyte-receptors to thereby bind the analyte-receptors to the sample-surface.

In particular, the method is suitable for manufacturing a biosensor device as described herein in the first aspect of the invention.

The method comprises forming a doped graphene layer structure on a substrate. Preferably, the graphene is formed by CVD on a surface of a substrate (which may be referred to as the growth surface of a substrate). Forming may be considered synonymous with synthesising, manufacturing, producing and growing.

CVD refers generally to a range of chemical vapour deposition techniques, each of which involve vacuum deposition to produce thin film materials such as two-dimensional crystalline materials like graphene. Volatile precursors, those in the gas phase or suspended in a gas, are decomposed to liberate the necessary species to form the desired material, carbon in the case of graphene.

CVD as described herein is intended to refer to thermal CVD such that the formation of graphene from the decomposition of a carbon-containing precursor is the result of the thermal decomposition of said carbon-containing precursor.

Preferably, the method involves forming graphene by thermal CVD such that decomposition is a result of heating the carbon-containing precursor. Doped graphene is formed from a carbon-containing precursor which also contains the doping element, in particular N and/or P. Alternatively, a further precursor containing the doping element may be simultaneously with the carbon-containing precursor (and may be carbon-containing itself). Preferably, the temperature of the growth surface during CVD is from 700° C. to 1350° C., preferably from 800° C. to 1250° C., more preferably from 1000° C. to 1250° C. The inventors have found that such temperatures are particularly effective for providing graphene growth directly on the materials described herein by CVD. Preferably, the CVD reaction chamber used in the method disclosed herein is a cold-walled reaction chamber wherein a heater coupled to the substrate is the only source of heat to the chamber.

In a particularly preferred embodiment, the CVD reaction chamber comprises a close-coupled showerhead having a plurality, or an array, of precursor entry points. Such CVD apparatus comprising a close-coupled showerhead may be known for use in MOCVD processes. Accordingly, the method may alternatively be said to be performed using an MOCVD reactor comprising a close-coupled showerhead. In either case, the showerhead is preferably configured to provide a minimum separation of less than 100 mm, more preferably less than 25 mm, even more preferably less than 10 mm, between the surface of the substrate and the plurality of precursor entry points. As will be appreciated, by a constant separation it is meant that the minimum separation between the surface of the substrate and each precursor entry point is substantially the same. The minimum separation refers to the smallest separation between a precursor entry point and the substrate surface (i.e. the surface of the metal oxide layer). Accordingly, such an embodiment involves a "vertical" arrangement whereby the plane containing the precursor entry points is substantially parallel to the plane of the substrate surface (i.e. the growth surface).

The precursor entry points into the reaction chamber are preferably cooled. The inlets, or when used, the showerhead, are preferably actively cooled by an external coolant, for example water, so as to maintain a relatively cool temperature of the precursor entry points such that the temperature of the precursor as it passes through the plurality of precursor entry points and into the reaction chamber is less than 100° C., preferably less than 50° C. For the avoidance of doubt, the addition of precursor at a temperature above ambient does not constitute heating the chamber, since it would be a drain on the temperature in the chamber and is responsible in part for establishing a temperature gradient in the chamber.

Preferably, a combination of a sufficiently small separation between the substrate surface and the plurality of precursor entry points and the cooling of the precursor entry points, coupled with the heating of the substrate to with a decomposition range of the precursor, generates a sufficiently steep thermal gradient extending from the substrate surface to the precursor entry points to allow graphene formation on the substrate surface. As disclosed in WO 2017/029470 (which is incorporated herein by reference with respect to the methods of forming nitrogen-containing graphene layers, as well as silicene and phosphorene), very steep thermal gradients may be used to facilitate the formation of high-quality and uniform graphene directly on non-metallic substrates, preferably across the entire surface of the substrate. The substrate may have a diameter of at least 5 cm (2 inches), at least 15 cm (6 inches) or at least 30 cm (12 inches). Particularly suitable apparatus for the method described herein include an Aixtron® Close-Coupled Showerhead® reactor and a Veeco® TurboDisk reactor. Such a method is particularly preferred for enabling the large-scale industrial manufacture of an array of biosensor devices upon a single common substrate. For the same reasons, the method is preferred for enabling the manufacture of multiple biosensor cells for a single biosensor device (or an array of biosensor devices which comprise multiple biosensor cells). This is particularly advantageous as this allows for consistent device fabrication with stable properties from one device to the next on a commercial scale.

Consequently, in a preferred embodiment, forming the doped graphene layer on the substrate comprises:

- providing a substrate on a heated susceptor in a CVD reaction chamber, the CVD reaction chamber having a plurality of cooled inlets arranged so that, in use, the inlets are distributed across the surface of the substrate and have constant separation from the surface of the substrate;
- cooling the inlets to less than 100° C.;
- introducing a carbon-containing precursor comprising nitrogen and/or phosphorus, and/or a carbon-containing precursor and/or a nitrogen-containing precursor and/or a phosphorus-containing precursor, in a gas phase and/or suspended in a gas through the inlets and into the CVD reaction chamber; and
- heating the susceptor to a temperature of at least 50° C. in excess of a decomposition temperature of the precursor, to provide a thermal gradient between the surface of the substrate and inlets that is sufficiently steep to thereby decompose the precursor and allow the formation of a doped graphene layer from carbon, and nitrogen and/or phosphorus, released from the decomposed precursor;

wherein the constant separation is less than 100 mm, preferably less than 25 mm, even more preferably less than 10 mm.

The presence of the carbon-containing precursor comprising nitrogen and/or phosphorus, or the nitrogen-containing or phosphorus-containing precursor leads to the production of the nitrogen-doped graphene layer structure. The extent of doping will depend on a number of factors which can be adjusted by the skilled person. Increasing the doping can be achieved with, for example, using a precursor which contains more N/P, and increasing the residency time of the precursor on the substrate surface (i.e. slightly higher pressure, slower rotation rate, higher precursor flow).

Preferably, the precursor is a single carbon-containing and nitrogen-containing precursor to thereby provide a nitrogen-doped graphene layer structure. Preferably, the precursor consists for carbon, hydrogen and nitrogen. Preferably, the carbon-containing precursor comprising nitrogen is a pyridine, diazine or triazine, or an alkylamine $NR_nH_{3-n}$, wherein R is a straight chain or branched alkyl group $C_mH_{2m+1}$, wherein n is from 1 to 3, and each m is independently from 1 to 6, preferably from 1 to 3.

Pyridine, diazine and triazine includes the parent molecules ($C_5H_5N$, $C_4H_4N_2$ and $C_3H_3N_3$) as well as substituted pyridine, diazine and triazine whereby one or more hydrogens are replaced with an R group, i.e. pyridine ($C_5H_{5-n}R_nN$), diazine ($C_4H_{4-n}R_nN$) or triazine ($C_3H_{3-n}R_nN$), where n is from 1 to 3 and optionally 4 for diazine and 4 or 5 for pyridine. Preferably, R is methyl (i.e. m is 1; —$CH_3$) The most common carbon-containing precursor in the art for graphene growth is methane ($CH_4$).

The inventors have found that it is preferable that the carbon-containing precursor used to form graphene is an organic compound, that is, a chemical compound, or molecule, that contains a carbon-hydrogen covalent bond, which comprises two or more carbon atoms. Such precursors have a lower decomposition temperature than methane which advantageously allows the growth of graphene at lower temperatures when using the method described herein which is particularly advantageous for growth on such non-metallic surfaces. Preferably, the precursor is a liquid when measured at 20° C. and 1 bar of pressure (i.e. under standard conditions according to IUPAC). Accordingly, the precursor has a melting point that is below 20° C., preferably below 10° C., and has a boiling point above 20° C., preferably above 30° C. Liquid precursors are simpler to store and handle when compared to gaseous precursors which typically require high pressure cylinders. Due to their relatively reduced volatility when compared to gaseous precursors, they present a lower safety risk during large scale manufacture. Increasing the molecular weight of the compounds beyond about $C_{10}$, particularly beyond about $C_{12}$, typically reduces their volatility and suitability for CVD growth of graphene on non-metallic substrates (though graphene can be produced from solid organic compounds).

It is also preferable that the organic compound comprise at least two methyl groups (—$CH_3$). Particularly preferred organic compounds for use as carbon-containing precursors, and methods of forming graphene therefrom by CVD, are described in UK Patent Application No. 2103041.6, the contents of which is incorporated herein in its entirety. The inventors have found that when forming graphene directly on non-metallic substrates, precursors beyond the traditional hydrocarbons methane and acetylene allow for the formation of even higher quality graphene, and by extension, doped graphene for use in the present invention. Preferably, the precursor is a $C_4$-$C_{10}$ organic compound, more preferably the organic compound is branched such that the organic compound has at least three methyl groups.

Preferably, where the precursor is an alkylamine, the precursor therefore preferably is a tertiary amine to provide three alkyl chains. Ethylamine, N-ethylmethylamine, diethylamine, N,N-dimethylethylamine, N,N-diethylmethylamine, and triethylamine are preferred alkylamines.

Preferably, the doped graphene layer structure of the biosensor device has a charge carrier density of less than $10^{13}$ $cm^{-2}$ (i.e. after covalent functionalisation with the linker moiety as measured under zero gate voltage and at room temperature, i.e. about 20° C.). Such a charge carrier density can be achieved through growth of a doped graphene layer structure by the method disclosed herein. The method is particularly advantageous in this regard since graphene-based sensors rely on having low charge carrier densities (but with high carrier mobilities) so as to benefit from the unique electronic properties of the two-dimensional material approaching charge neutrality. The present inventors have also found that the doped graphene layer structure may have a charge carrier mobility of greater than 4,000 $cm^2/Vs$, preferably greater than 6,000 $cm^2/Vs$, more preferably greater than 8000 $cm^2/Vs$.

In some embodiments of the present invention, a majority of the nitrogen is graphitic nitrogen (i.e. at least 50 at %). Such an embodiment is advantageous because, without wishing to be bound by theory, graphitic nitrogen is n-type doping and subsequent functionalisation of such nitrogen shifts to p-type doping. As a result, the method enables a product with a low charge carrier density to be manufactured which is desirable for sensing applications.

The graphene formed on the substrate is then patterned using conventional techniques to form a doped graphene layer structure. In one preferred embodiment, the graphene is patterned using laser etching (for example, as described in WO 2019/138232 A1), or by plasma etching, preferably oxygen plasma etching.

The method further comprises providing at least first and second electrical contacts on the doped graphene layer structure to define a sample-surface between said electrical contacts. The contacts are provided so as to enable the device to be incorporated into a circuit. Electrical contacts are preferably metal contacts, preferably comprising one or more of titanium, aluminium, chromium and gold. Preferably, the contacts are titanium and/or gold metal contacts. The contacts may be formed by any standard technique such as electron beam deposition, preferably using a mask. Preferably, the contacts are provided at distal edges of the patterned graphene. The contacts define a sample-surface of the graphene layer structure through which an electrical current will flow which itself will be modulated by the presence of the analyte to be tested for when in use.

The doped graphene layer structure is then functionalised by a two-step process whereby the doped graphene layer structure is first reacted with linker molecules to covalent bond a linker molecule to each nitrogen and/or phosphorus dopant. Typically, a solution comprising the linker precursor molecule is applied to the doped graphene surface (i.e. a plurality of linker precursor molecules, for example, a stoichiometric excess).

Secondly, the linker precursor molecule covalent bound the dopant of the graphene layer structure is then reacted with an analyte-receptor so as to bind the analyte-receptor to the graphene via the linker moiety. Preferably, the analyte-receptor is similarly bound the linker molecule via a covalent bond. For example, a free amine of an appropriate analyte-receptor may undergo an equivalent covalent reaction to form an amide with the linker moiety.

Consequently, it is preferred that either or both reactions involve the formation of an amide functional group (i.e. an amidation reaction). Such functionalisation of the doped graphene layer structure may be achieved using the linker precursor molecules described hereinabove. In other embodiments, the doped graphene may be functionalised by N- or P-alkylation reactions, typically with an alkyl halide, such as an alkyl bromide, further comprising an appropriate functional group for bind the analyte-receptor in the second reaction thereafter.

In a further aspect there is provided a method of testing a sample composition for a predetermined analyte, the method comprising:

- providing a biosensor device as described herein, wherein the analyte-receptors are sensitive to the presence of the predetermined analyte;
- contacting the sample-surface with the sample composition; and
- observing an electrical output between the first and second electrical contacts to determine whether or not the sample composition comprises the predetermined analyte.

The method comprises using a biosensor device as described herein which comprises an appropriate analyte-receptor for the biorecognition of a predetermined analyte. The sample composition may be any typical composition for testing. For example, a sample may derive from a human or animal, such as a blood, urine, saliva, sweat, tears, faeces, breath, plasma, or sperm sample. In other embodiments, the sample composition is a food sample, an environmental sample (e.g. river, sea or waste water, ground or soil samples) or may be of plant origin (e.g. tree or crop samples). Preparation of suitable samples is well known; water samples may be used directly, whereas other samples may be dissolved in an appropriate solvent (e.g. water) and filtered as necessary for testing.

The composition is contacted with the sample-surface of the doped graphene layer structure so that, upon interaction with the analyte, if present in the sample composition, an electrical current provided by the contacts and through the doped graphene will be modulated. Thus, by observing an electrical output between the contacts, a user may determine whether the predetermined analyte (as determined by the nature of the analyte-receptor of the biosensor device) is present in the sample composition. For example, a positive or negative result may be determined by the conductance of the graphene exceeding a predetermined threshold.

In a first step, a nitrogen-doped graphene monolayer 100 is grown by CVD in a close-coupled reaction chamber, directly on a sapphire substrate (not shown) from a triethyl amine carbon- and nitrogen-containing precursor. The nitrogen-doped graphene monolayer 100 consists substantially of carbon and nitrogen atoms. FIG. 1 illustrates a “cut-out” of the graphene monolayer 100. As will be appreciated, the graphene monolayer may be much larger comprising a plurality of nitrogen atoms uniformly distributed throughout the graphene monolayer. As illustrated by the cut-out, the graphene monolayer 100 comprises 1 nitrogen atom for every 56 carbon atoms (i.e. about 1.75 at % doping). The nitrogen is present as graphitic nitrogen.

The method of manufacturing a biosensor device comprises a step of depositing metal contacts (not shown) so as to define a sample-surface between said contacts. Preferably, such a step is carried out before step 200 of reacting the nitrogen-doped graphene monolayer 100 with SuO-[PEG]$_x$—COOH 105 (i.e. a plurality of linker precursor molecules) to covalently bond each linker precursor molecule to a nitrogen atom thereby forming an intermediate functionalised graphene layer structure 115. The linker precursor molecule 105 comprises a polyethylene glycol linker spacer moiety ([PEG]x) which then separates the nitrogen-doped graphene layer structure from the analyte-receptor (via appropriate functional groups) once functionalised. The linker precursor molecule 105 further comprises a carboxylic acid moiety at the distal end of the polyethylene glycol spacer. The reaction 200 comprises converting 205 the carboxylic acid group to an acyl halide and reacting the acyl halide 110 with a nitrogen atom of the graphene layer structure 100 by an amidation reaction thereby forming an amide.

In step 210, the intermediate functionalised graphene layer structure 115 is reacted with a free terminal amine (—$NH_2$) of a single stranded aptamer 120. Such amide coupling protocols are known in the art. The reaction in step 210 provides the analyte-receptor aptamer covalently bonded to the linker moiety to bind the aptamer 120 with the nitrogen of the nitrogen-doped graphene layer structure 125.

FIG. 2 is an illustration of the nitrogen species present in nitrogen doped graphene. Graphitic nitrogen is three-coordinate and is represented by N. Pyridinic nitrogen is two-coordinate in a six-membered ring and is represented by N'. Pyrrolic nitrogen is two-coordinate in a five-membered ring and is represented by N".

The present invention will be described further with reference to the following clauses:

Clause 1. A biosensor device comprising:

- a doped graphene layer structure having at least first and second electrical contacts and a sample-surface between said electrical contacts for receiving an analyte composition to be tested;
- wherein the doped graphene layer structure is doped with nitrogen and/or phosphorus atoms in an amount of from 1 at % to 10 at %; and
- wherein the sample-surface is functionalised with a plurality of analyte-receptors, each analyte-receptor being bound to a nitrogen or phosphorus atom of the doped graphene layer structure by a covalent linker moiety.

Clause 2. The biosensor according to clause 1, wherein the doped graphene layer structure is doped with nitrogen and/or phosphorus atoms in an amount of from 2 at % to 7.5 at %, preferably from 3 at % to 5 at %.

Clause 3. The biosensor according to clause 1 or clause 2, wherein the doping consists of nitrogen atoms.

Clause 4. The biosensor according to any preceding clause, further comprising a non-metallic substrate, wherein the doped graphene layer structure is provided on the substrate.

Clause 5. The biosensor according to clauses 4, wherein the doped graphene layer structure is obtained by CVD growth directly on the substrate, preferably using a carbon-containing precursor comprising nitrogen.

Clause 6. The biosensor according to clause 4 or clause 5, wherein the substrate comprises silicon, silicon carbide, silicon nitride, silicon dioxide, sapphire, hafnium dioxide, yttria-stabilised zirconia, magnesium aluminate, yttrium orthoaluminate, strontium titanate, calcium difluoride, germanium and/or a III/V semiconductor.

Clause 7. The biosensor according to any preceding clause, wherein the doped graphene layer structure has a charge carrier density of less than $10^{12}$ $cm^2$.

Clause 8. The biosensor according to any preceding clause, wherein the doped graphene layer structure has a charge carrier mobility of greater than 4,000 $cm^2$/Vs, preferably greater than 6,000 $cm^2$/Vs, more preferably greater than 8000 $cm^2$/Vs.

Clause 9. The biosensor according to any preceding clause, wherein each linker moiety is covalently bonded to the nitrogen via a carbonyl group thereby forming an amide functional group.

Clause 10. The biosensor according to any preceding clause, wherein each analyte-receptor is covalently bonded to the linker moiety, preferably via an amide functional group.

Clause 11. The biosensor according to any preceding clause, wherein each linker moiety comprises a polyethylene glycol spacer.

Clause 12. A method of manufacturing a biosensor device, the method comprising:

forming a doped graphene layer on a substrate, the graphene layer doped with nitrogen and/or phosphorus atoms in an amount of from 1 at % to 10 at %;

patterning the doped graphene layer to form a doped graphene layer structure;

providing at least first and second electrical contacts on the doped graphene layer structure to define a sample-surface between said electrical contacts; and functionalising the doped graphene layer structure by:

(i) reacting the doped graphene layer structure with a plurality of linker precursor molecules to covalently bond each linker precursor molecule to a nitrogen or phosphorus atom of the doped graphene layer structure; and (ii) reacting the covalently bonded linker precursor molecules with a plurality of analyte-receptors to thereby bind the analyte-receptors to the sample-surface.

Clause 13. The method according to clause 12, wherein step (ii) of reacting the linker precursor molecules with a plurality of analyte-receptors comprises reacting the linker precursor molecules with a plurality of analyte-receptors to covalently bond each analyte-receptor with a linker precursor molecule.

Clause 14. The method according to clause 12 or clause 13, wherein the step (i) of reacting the doped graphene layer structure and/or step (ii) of reacting the linker precursor molecules comprises an amidation reaction.

Clause 15. The method according to any of clauses 12 to 14, wherein the step of forming the doped graphene layer on the substrate comprises:

providing the substrate on a heated susceptor in a CVD reaction chamber, the CVD reaction chamber having a plurality of cooled inlets arranged so that, in use, the inlets are distributed across the surface of the substrate and have constant separation from the surface of the substrate;

cooling the inlets to less than 100° C.;

introducing a carbon-containing precursor comprising nitrogen and/or phosphorus, and/or a carbon-containing precursor and/or a nitrogen-containing precursor and/or a phosphorus-containing precursor, in a gas phase and/or suspended in a gas through the inlets and into the CVD reaction chamber; and heating the susceptor to a temperature of at least 50° C. in excess of a decomposition temperature of the precursor, to provide a thermal gradient between the surface of the substrate and inlets that is sufficiently steep to thereby decompose the precursor and allow the formation of a doped graphene layer from carbon and nitrogen released from the decomposed precursor;

wherein the constant separation is less than 100 mm, preferably less than 25 mm, even more preferably less than 10 mm.

Clause 16. The method according to clause 15, wherein the carbon-containing precursor comprising nitrogen is a pyridine, diazine or triazine, or an alkylamine $NR_nH_{3-n}$, wherein R is a straight chain or branched alkyl group $C_mH_{2m+1}$, wherein n is from 1 to 3, and each m is independently from 1 to 6, preferably from 1 to 3.

Clause 17. A method of testing a sample composition for a predetermined analyte, the method comprising:

providing a biosensor device according to any of clauses 1 to 11, wherein the analyte-receptors are sensitive to the presence of the predetermined analyte;

contacting the sample-surface with the sample composition; and observing an electrical output between the first and second electrical contacts to determine whether or not the sample composition comprises the predetermined analyte.

As used herein, the singular form of "a", "an" and "the" include plural references unless the context clearly dictates otherwise. The use of the term "comprising" is intended to be interpreted as including such features but not excluding other features and is also intended to include the option of the features necessarily being limited to those described. In other words, the term also includes the limitations of "consisting essentially of" (intended to mean that specific further components can be present provided they do not materially affect the essential characteristic of the described feature) and "consisting of" (intended to mean that no other feature may be included such that if the components were expressed as percentages by their proportions, these would add up to 100%, whilst accounting for any unavoidable impurities), unless the context clearly dictates otherwise.

It will be understood that, although the terms "first", "second", etc. may be used herein to describe various elements, layers and/or portions, the elements, layers and/or portions should not be limited by these terms. These terms are only used to distinguish one element, layer or portion from another, or a further, element, layer or portion. It will be understood that the term "on" is intended to mean "directly on" such that there are no intervening layers between one material being said to be "on" another material. Spatially relative terms, such as "under", "below", "beneath", "lower", "over", "above", "upper" and the like, may be used herein for ease of description to describe one element or feature's relationship to another element(s) or feature(s). It will be understood that the spatially relative terms are intended to encompass different orientations of the device in use or operation in addition to the orientation depicted in the figures. For example, if a device as described herein is turned over, elements described as "under" or "below" other elements or features would then be oriented "over" or "above" the other elements or features. Thus, the example term "under" can encompass both an orientation of over and under. The device may be otherwise oriented and the spatially relative descriptors used herein interpreted accordingly.

The foregoing detailed description has been provided by way of explanation and illustration, and is not intended to limit the scope of the appended claims. Many variations of the presently preferred embodiments illustrated herein will be apparent to one of ordinary skill in the art, and remain within the scope of the appended claims and their equivalents.

The invention claimed is:

1. A biosensor device comprising:

a doped graphene layer structure having at least first and second electrical contacts and a sample-surface between said electrical contacts for receiving an analyte composition to be tested;

wherein the doped graphene layer structure is doped with nitrogen atoms in an amount of from 1 at % to 10 at %; and wherein the sample-surface is functionalised with a plurality of analyte-receptors, each analyte-receptor being bound to a nitrogen atom of the doped graphene layer structure by a covalent linker moiety, wherein each linker moiety is covalently bonded to the nitrogen via carbonyl group thereby forming an amide functional group.

2. The biosensor according to claim 1, wherein the doped graphene layer structure is doped with nitrogen atoms in an amount of from 2 at % to 7.5 at %.

3. The biosensor according to claim 1, wherein the doping consists of nitrogen atoms.

4. The biosensor according to claim 1, further comprising a non-metallic substrate, wherein the doped graphene layer structure is provided on the substrate.

5. The biosensor according to claim 4, wherein the doped graphene layer structure is obtained by CVD growth directly on the substrate.

6. The biosensor according to claim 4, wherein the doped graphene layer structure is obtained by CVD growth directly on the substrate using a carbon containing precursor comprising nitrogen.

7. The biosensor according to claim 4, wherein the substrate comprises silicon, silicon carbide, silicon nitride, silicon dioxide, sapphire, hafnium dioxide, yttria-stabilised zirconia, magnesium aluminate, yttrium orthoaluminate, strontium titanate, calcium difluoride, germanium and/or a III/V semiconductor.

8. The biosensor according to claim 1, wherein the doped graphene layer structure has a charge carrier density of less than $10^{12}$ $cm^{-2}$.

9. The biosensor according to claim 1, wherein the doped graphene layer structure has a charge carrier mobility of greater than 4,000 $cm^2/Vs$.

10. The biosensor according to claim 1, wherein each analyte-receptor is covalently bonded to the linker moiety.

11. A method of manufacturing the biosensor device according to claim 1, the method comprising:

forming a doped graphene layer on a substrate, the graphene layer doped with nitrogen atoms in an amount of from 1 at % to 10 at %;

patterning the doped graphene layer to form a doped graphene layer structure;

providing at least first and second electrical contacts on the doped graphene layer structure to define a sample-surface between said electrical contacts; and functionalising the doped graphene layer structure by:

(i) reacting the doped graphene layer structure with a plurality of linker precursor molecules using an amidation reaction to covalently bond each linker precursor molecule to a nitrogen atom of the doped graphene layer structure; and (ii) reacting the covalently bonded linker precursor molecules with a plurality of analyte-receptors to thereby bind the analyte-receptors to the sample-surface.

12. The method according to claim 11, wherein step (ii) of reacting the linker precursor molecules with a plurality of analyte-receptors comprises reacting the linker precursor molecules with a plurality of analyte-receptors to covalently bond each analyte-receptor with a linker precursor molecule.

13. The method according to claim 11, wherein the step (ii) of reacting the linker precursor molecules comprises an amidation reaction.

14. The method according to claim 11, wherein the step of forming the doped graphene layer on the substrate comprises:

providing the substrate on a heated susceptor in a CVD reaction chamber, the CVD reaction chamber having a plurality of cooled inlets arranged so that, in use, the inlets are distributed across the surface of the substrate and have constant separation from the surface of the substrate;

cooling the inlets to less than 100° C.;

introducing a carbon-containing precursor comprising nitrogen, and/or a carbon-containing precursor and a nitrogen-containing precursor, in a gas phase and/or suspended in a gas through the inlets and into the CVD reaction chamber; and heating the susceptor to a temperature of at least 50° C. in excess of a decomposition temperature of the precursor, to provide a thermal gradient between the surface of the substrate and inlets that is sufficiently steep to thereby decompose the precursor and allow the formation of a doped graphene layer from carbon and nitrogen released from the decomposed precursor;

wherein the constant separation is less than 100 mm.

15. The method according to claim 14, wherein the carbon-containing precursor comprising nitrogen is a pyridine, diazine or triazine, or an alkylamine $NR_nH_{3-n}$, wherein R is a straight chain or branched alkyl group $C_mH_{2m+1}$, wherein n is from 1 to 3, and each m is independently from 1 to 6.

16. A method of testing a sample composition for a predetermined analyte, the method comprising:

providing a biosensor device according to claim 1, wherein the analyte-receptors are sensitive to the presence of the predetermined analyte;

contacting the sample-surface with the sample composition; and observing an electrical output between the first and second electrical contacts to determine whether or not the sample composition comprises the predetermined analyte.

17. The biosensor according to claim 1, wherein the doped graphene layer structure is doped with nitrogen atoms in an amount of from 3 at % to 5 at %.

18. The biosensor according to claim 1, wherein the doped graphene layer structure has a charge carrier mobility of greater than 6,000 $cm^2/Vs$.

19. A biosensor device comprising:

a doped graphene layer structure having at least first and second electrical contacts and a sample-surface between said electrical contacts for receiving an analyte composition to be tested;

wherein the doped graphene layer structure is doped with nitrogen and/or phosphorus atoms in an amount of from 1 at % to 10 at %; and wherein the sample-surface is functionalised with a plurality of analyte-receptors, each analyte-receptor being bound to a nitrogen or phosphorus atom of the doped graphene layer structure by a covalent linker moiety, wherein each linker moiety comprises a polyethylene glycol spacer.

20. The biosensor according to claim 19, wherein the doped graphene layer structure is doped with nitrogen atoms in an amount of from 3 at % to 5 at %.

* * * * *